(12) United States Patent
McCormack et al.

(10) Patent No.: US 10,910,281 B2
(45) Date of Patent: Feb. 2, 2021

(54) INTEGRATED CIRCUIT METALLIC ION DIFFUSION DEFECT VALIDATION

(71) Applicant: Microsoft Technology Licensing, LLC, Redmond, WA (US)

(72) Inventors: Mark Thomas McCormack, Livermore, CA (US); Louis Charles Kordus, II, Los Altos, CA (US); Anik Mehta, Livermore, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 196 days.

(21) Appl. No.: 16/256,395

(22) Filed: Jan. 24, 2019

(65) Prior Publication Data

US 2020/0243403 A1 Jul. 30, 2020

(51) Int. Cl.
*H01L 21/66* (2006.01)
*G01N 33/20* (2019.01)

(52) U.S. Cl.
CPC ............. *H01L 22/14* (2013.01); *G01N 33/20* (2013.01); *H01L 22/12* (2013.01); *H01L 22/20* (2013.01)

(58) Field of Classification Search
CPC .......... H01L 22/14; H01L 22/12; H01L 22/20
See application file for complete search history.

(56) References Cited

U.S. PATENT DOCUMENTS

| | | |
|---|---|---|
| 5,895,274 A | 4/1999 | Lane et al. |
| 6,617,176 B1 | 9/2003 | Sanchez et al. |
| 7,601,541 B2 * | 10/2009 | Mohammad ......... G01N 23/223 436/80 |
| 7,888,142 B2 | 2/2011 | Burnham et al. |
| 2005/0274805 A1 | 12/2005 | Ramappa |
| 2009/0047748 A1 | 2/2009 | Savtchouk et al. |

FOREIGN PATENT DOCUMENTS

JP     H0964133 A     3/1997

OTHER PUBLICATIONS

Bartsch, et al., "Quick Determination of Copper-Metallization Long-Term Impact on Silicon Solar Cells", In Journal of The Electrochemical Society, vol. 157, Issue 10, Aug. 13, 2010, 5 Pages.
"International Search Report and Written Opinion Issued in PCT Application No. PCT/US20/012288", dated May 6, 2020, 11 Pages.
Raghavan, et al., "Diffusion of Copper through Dielectric Films under Bias Temperature Stress", In Journal of Thin Solid Films, vol. 262, Issues 1-2, Jun. 15, 1995, pp. 168-176.

(Continued)

*Primary Examiner* — Selim U Ahmed
(74) *Attorney, Agent, or Firm* — Alleman Hall Creasman & Tuttle LLP

(57) ABSTRACT

A method for validating that an integrated circuit die is not susceptible to a conductive metallic ion diffusion defect is disclosed. A test component is applied to a backside surface of the integrated circuit die to form a test assembly. The test component includes a conductive metal layer and a transport media layer for facilitating diffusion of conductive metallic ions. The test assembly is heated at a thermal activation temperature. The integrated circuit die is computer validated to determine whether or not the integrated circuit die has the conductive metallic ion diffusion defect.

20 Claims, 5 Drawing Sheets

(56) References Cited

OTHER PUBLICATIONS

Kot, et al., "Development of a Storage Getter Test for Cu Contaminations in Silicon Wafers Based on ToF-SIMS Measurements", In Journal of Acta Physica Polonica A, vol. 125, No. 4, Apr. 2014, pp. 965-968.

Lee, et al., "Impacts of Cu Contamination on Device Reliabilities in 3-D IC Integration", In Journal of IEEE Transactions on Device and Materials, vol. 14, Issue 1, Mar. 2014, pp. 451-462.

Polignano, et al., "Revealing Copper Contamination in Silicon after Low Temperature Treatments", In Journal of ECS Transactions, vol. 25, Issue 3, Sep. 25, 2009, pp. 337-348.

\* cited by examiner

INTEGRATED CIRCUIT METALLIC ION DIFFUSION DEFECT VALIDATION

BACKGROUND

In some cases, conductive metallic ions (such as those containing copper (Cu)) may undesirably diffuse through layers of an integrated circuit die, e.g., from the backside of the integrated circuit die. Such conductive metallic ion diffusion may cause failures at affected portions of the integrated circuit die. For example, undesirable conductive metallic ion diffusion may cause transistors in the integrated circuit die to short circuit during operation. In some cases, such undesirable conductive metallic ion diffusion may be a result of a manufacturing flaw of the integrated circuit die.

SUMMARY

An accelerated method for validating that an integrated circuit die is not susceptible to a conductive metallic ion diffusion defect is disclosed. A test component is applied to a backside surface of the integrated circuit die to form a test assembly. The test component includes a conductive metal layer and a transport media layer for facilitating diffusion of conductive metallic ions. The test assembly is heated at a thermal activation temperature. The integrated circuit die is computer validated to determine whether or not the integrated circuit die has the conductive metallic ion diffusion defect.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
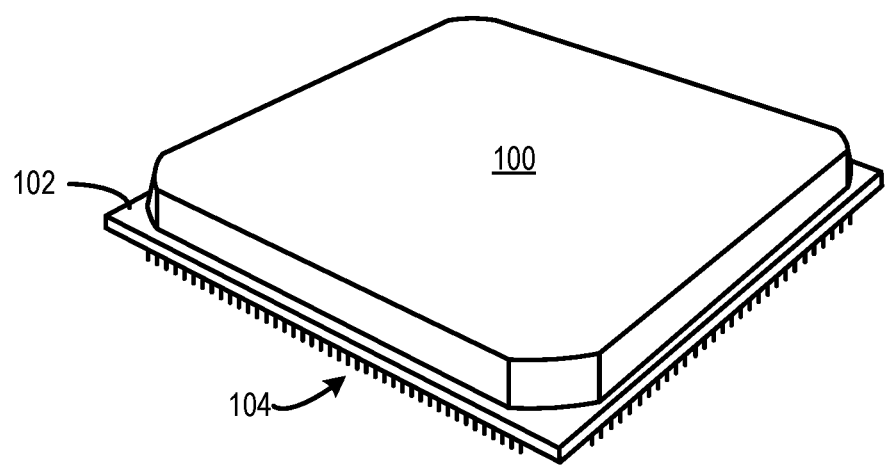
FIG. 1 shows a perspective view of an example integrated circuit die.

FIG. 1 shows an example integrated circuit die 100 mounted to a substrate package 102. The substrate package 102 includes a plurality of contacts 104. The contacts 104 may be connected to a hardware package, such as a motherboard, to install the integrated circuit die 100 in a computing device for operation. Non-limiting examples of different types of integrated circuit dies include a central processing unit (CPU), a graphics processing unit (GPU), a system on a chip (SoC), and a memory unit, among other types. The integrated circuit die 100 may take any suitable form.

Figure 2:
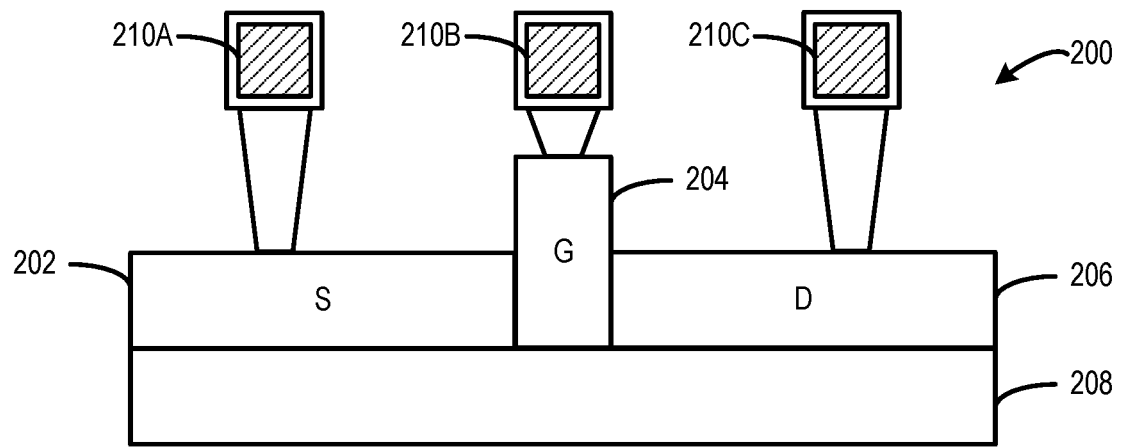
FIG. 2 shows a cross-sectional view of aspects of an integrated circuit die that is free from conductive metallic ion diffusion defects.

FIG. 2 schematically shows a cross-sectional view of aspects of an exemplary integrated circuit die. More particularly, different layers of an integrated circuit die that form a transistor 200 are depicted. The transistor 200 includes a source 202, a gate 204, and a drain 206 that are formed on a substrate layer 208. A plurality of interconnects 210 (e.g., 210A, 210B, 210C) are electrically connected to the source 202, the gate 204, and the drain 206, respectively. The interconnects 210 comprise conductive metal that facilitates electrical connections between the transistor 200 and other electronic components of the integrated circuit die. Such electrical connections allow for the transmission and distribution of electrical signals and power across the integrated circuit die. In one example, the conductive metal is or includes copper.

In some cases, conductive metallic ions may undesirably diffuse through layers of an integrated circuit die, e.g., from the backside of the die, and cause failures of affected portions of the integrated circuit die. For example, as shown in FIG. 2, a plurality of foreign metallic ions may create shorts from either the source 202, the gate 204 or the drain 206 to the substrate 208, or to each other. Note that the depicted schematic example is simplified/idealized for purposes of clarity, and a conductive metallic ion diffusion defect in an integrated circuit die may take any suitable form resulting from undesirable migration of conductive material.

The undesirable diffusion of conductive metallic ions in an integrated circuit die may not always be readily identifiable upon manufacturing of the integrated circuit die. For example, although an integrated circuit die may be susceptible to a conductive metallic ion diffusion defect, the negative effects of such a defect may not present themselves until after the integrated circuit die has been put into operation for a certain amount of time. As such, it may be difficult to detect that an integrated circuit die is susceptible to a conductive metallic ion diffusion defect prior to the integrated circuit die being put into operation.

Accordingly, the present description is directed to an approach for validating that an integrated circuit die is not susceptible to a conductive metallic ion diffusion defect. The validation approach may accelerate conductive metallic ion diffusion in an integrated circuit die that is susceptible to the conductive metallic ion diffusion defect by employing a combination of acceleration techniques. In one example, the validation approach includes applying a test component to a backside surface of an integrated circuit die under test to form a test assembly. The test component includes a conductive metal layer and a transport media layer. The conductive metal layer provides a significant source of conductive metal that may be ionized during the validation approach to contribute to the diffusion of conductive metallic ions through the integrated circuit die under test. The transport media layer may facilitate the diffusion of the conductive metallic ions through the susceptible portions of the integrated circuit die under test. Furthermore, as part of the validation process, the test assembly is heated at a thermal activation temperature that facilitates conductive metallic ions to be transported via the transport media between the conductive metal layer and the susceptible portions of the integrated circuit die to expose the defect in the integrated circuit die.

In this way, an integrated circuit die that is susceptible to conductive metallic ion diffusion defects can be identified in a timely manner, allowing integrated circuit dies to be efficiently validated prior to being put into operation in computing devices.

Figure 3:
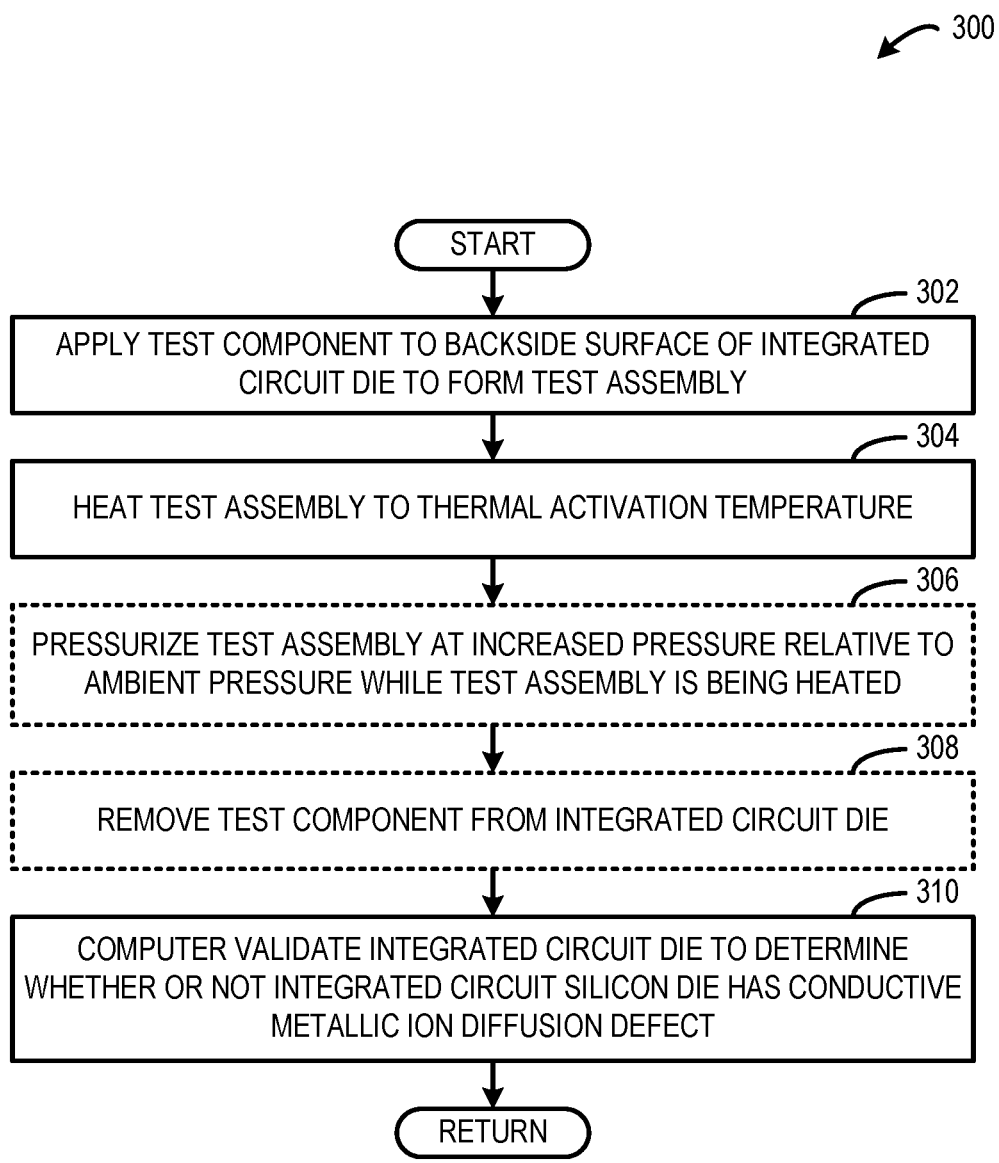
FIG. 3 is a flowchart of an example method for validating that an integrated circuit die is not susceptible to a conductive metallic ion diffusion defect.

FIG. 3 is a flowchart of an example method 300 for validating that an integrated circuit die is not susceptible to a conductive metallic ion diffusion defect. The validation method 300 may be performed as a screening process that is separate from a manufacturing process of the integrated circuit die (e.g., a post-manufacturing validation). At 302, the method 300 may include applying a test component to a backside surface of an integrated circuit die to form a test assembly.

Figure 4:
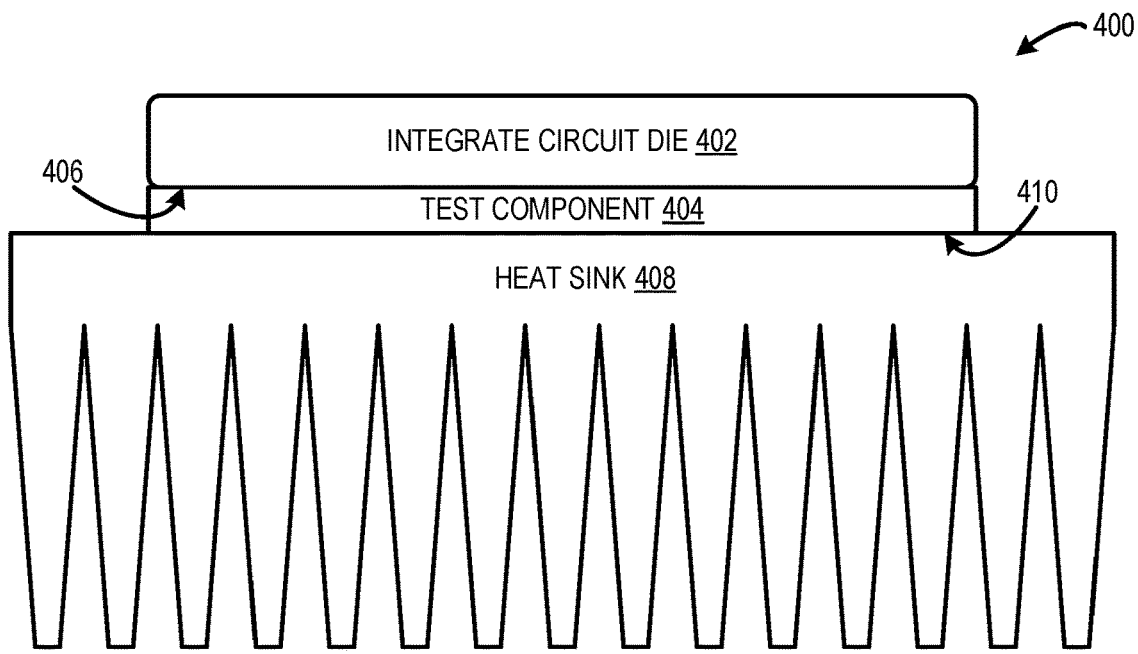
FIG. 4 schematically shows an example test assembly.

FIG. 4 schematically shows an example test assembly 400 that may be formed to validate that an integrated circuit die is not susceptible to a conductive metal diffusion defect. The test assembly 400 includes an integrated circuit die 402 under test. A test component 404 is applied to a backside surface 406 of the integrated circuit die 402. The test component 404 may form a layer that covers substantially the entire backside surface 406 of the integrated circuit die 402. The test component 404 may include a conductive metal and a transport media. The conductive metal included in the test component 404 may be matched to a conductive metal of the integrated circuit die 402. For example, if the integrated circuit die 402 may be susceptible to a copper diffusion defect, then the test component may be configured to include copper. The transport media may include any suitable material that is configured to be inserted between two components in order to enhance the thermal coupling between the two components. In particular, the transport media may be configured to facilitate ionization of the conductive metal such that the conductive metal ions may diffuse between the test component 404 and the integrated circuit die 402. In some examples, the transport media may include a thermal interface material. Non-limiting examples of thermal interface face materials that may be included in the test component 404 include thermal grease, thermal adhesive, a thermally conductive pad, a thermal tape, and phase-change materials.

Figure 5:
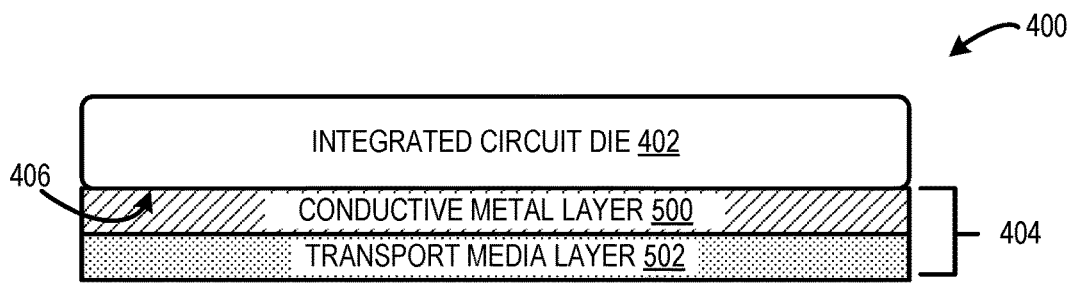
FIG. 5 schematically shows an example test component within a test assembly.

In some implementations, the conductive metal and the transport media of the test component 404 may be arranged into different layers. In some examples, as shown in FIG. 5, the test component 404 may include a conductive metal layer 500 that is applied directly to the backside surface 406 of the integrated circuit die 402. In some examples, the conductive metal layer 500 may be applied to substantially the entire backside surface 406 of the integrated circuit die 402. The conductive metal layer 500 may comprise any suitable conductive metal material. In one example, the conductive metal layer 500 comprises copper. The conductive metal layer 500 may have any suitable thickness. In one example, the conductive metal layer 500 may a have a thickness ranging between 0.0001-0.002 millimeters.

Furthermore, a transport media layer 502 may be applied directly to the conductive metal layer 500 to form the test component 404. In some examples, the transport media layer 502 may be applied to substantially the entire surface of the conductive metal layer 500. In some examples, the transport media layer 502 may have a surface area that is greater than or equal to a surface area of the conductive metal layer 500. The transport media layer 502 may have any suitable thickness. Moreover, the thickness of the transport media layer 502 may depend on the type of transport media that is used in the test component 404. The depicted example may be preferred for use in the validation process, because the surface contact between the conductive metal layer and the backside surface of the integrated circuit die may be sufficiently high to promote diffusion of conductive metallic ions between the test component 404 and the integrated circuit die 402.

Figure 6:
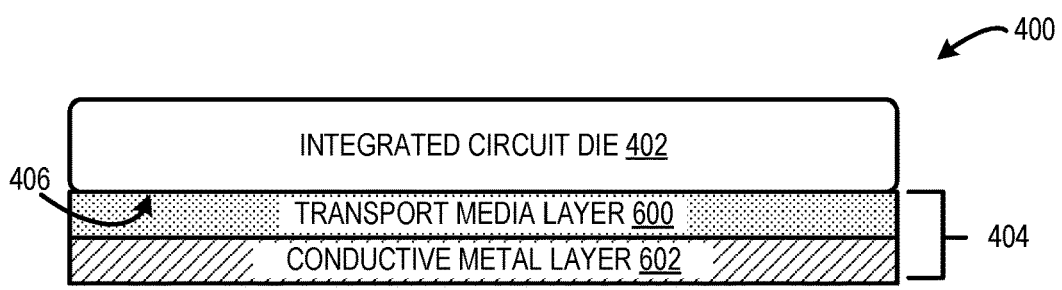
FIG. 6 schematically shows another example test component within a test assembly.

Alternatively, in some examples, as shown in FIG. 6, the test component 404 may include a transport media layer 600 that is applied directly to the backside surface 406 of the integrated circuit die 402. In some examples, the transport media layer 600 may be applied to substantially the entire backside surface 406 of the integrated circuit die 402. Furthermore, a conductive metal layer 602 may be applied directly to the transport media layer 600 to form the test component 404. In some examples, the conductive metal layer 602 may be applied to substantially the entire surface of the transport media layer 600. In some examples, the transport media layer 602 may have a surface area that is greater than or equal to a surface area of the conductive metal layer 500.

Returning to FIG. 4, in some implementations, the test assembly 400 optionally may include a heat sink 408. The heat sink 408 may be applied to a backside surface 410 of the test component 404. In particular, the heat sink 408 may be clamped to the integrated circuit die 402 to compress the test component 404 to the backside surface 406 of the integrated circuit die 402. In this way, surface contact between the test component 404 and the integrated circuit die 402 may be increased to better facilitate diffusion of conductive metallic ions between the test component 404 and the integrated circuit die 402.

Figure 7:
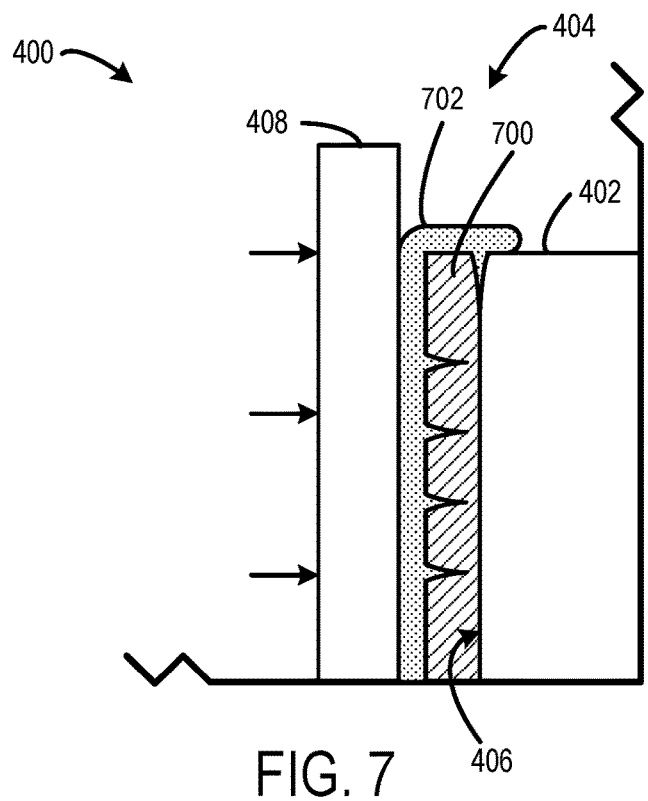
FIG. 7 schematically shows aspects of a test assembly.

FIG. 7 schematically shows aspects of the test assembly 400 including the heat sink 408. In particular, when the heat sink 408 is clamped to the integrated circuit die 402, the heat sink 408 compresses the test component 404 causing the conductive metal layer 700 to press against the backside surface 406 of the integrated circuit die 402 to increase surface contact between the two surfaces. Furthermore, in some examples, the transport media layer 702 may be a viscous material. In some such examples, the heat sink 408 may compress the transport media layer 702 causing the transport media to envelope the circumference of the conductive metal layer 700. In particular, the transport media may be pressed around the outer edges of the conductive metal layer 700 in between the backside surface 406 and the conductive metal layer 700. Such a spatial arrangement of the different components of the test assembly 400 may further promote ionization of the conductive metal and diffusion of the conductive metallic ions from the conductive metal layer 700 into the integrated circuit die 402.

Returning to FIG. 3, at 304, the method 300 includes heating the test assembly to a thermal activation temperature. For example, the test assembly may be placed in an oven to heat the test assembly to the thermal activation temperature. The thermal activation temperature may be a temperature that is suitable to promote diffusion of conductive metallic ions throughout the integrated circuit die under test. In some examples, the thermal activation temperature may be a temperature at which the transport media changes phase (e.g., becomes more viscous or at least partially liquifies to promote transport of conductive metallic ions). In order to accelerate any potential diffusion of conductive metallic ions throughout the integrated circuit die under test, in some examples, the thermal activation temperature may be set such that it is greater than an operating temperature of the integrated circuit die. This may allow diffusion to occur more quickly than it would occur during normal operation of the integrated circuit die. For example, the thermal activation temperature may be selected from a thermal range of 100-150 degrees Celsius. In one particular example, the thermal activation temperature is 125 degrees Celsius.

Furthermore, in some examples, the test assembly may be heated to the thermal activation temperature for a designated duration that is suitable to promote diffusion of conductive metallic ions throughout the integrated circuit die under test. For example, the designated duration may be is selected from a temporal range of 72-120 hours. In one particular example, the test assembly is heated to the thermal activation temperature for 96 hours.

In some implementations, at 306, the method 300 optionally may include pressurizing the test assembly at an increased pressure relative to an ambient pressure while the test assembly is being heated to the thermal activation temperature. For example, the test assembly may be heated and pressurized in an autoclave or some other heated pressure chamber. The test assembly may be pressurized in addition to being heated to further hasten the diffusion of conductive metallic ions in the integrated circuit die under test. In some examples, the test assembly may be pressurized for substantially the entire duration that the test assembly is heated. In other examples, the test assembly may be pressurized for a portion of the duration that the test assembly is heated.

Figure 8:
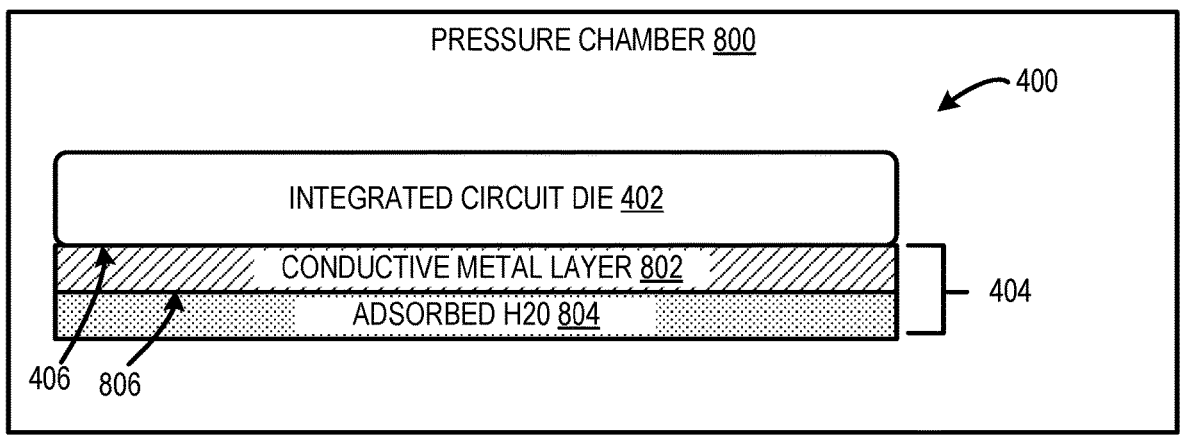
FIG. 8 schematically shows another example test component configured for use in a pressure-based validation method.

In some implementations in which the test assembly is pressurized, the transport media of the test component that is applied to the integrated circuit die under test may be a liquid that forms a film on the test assembly once the test assembly is pressurized. For example, as shown in FIG. 8, a conductive metal layer 802 may be applied to the backside surface 406 of the integrated circuit die 402 under test to form a test assembly 400. The test assembly 400 may be placed in a pressure chamber 800 and pressurized. The pressurization may cause an adsorbed $H_2O$ layer 804 to form on the exposed backside surface 806 of the conductive metal layer 802. The adsorbed $H_2O$ layer 804 may act as a transport media layer that facilitates the diffusion of conductive metallic ions between the conductive metal layer 802 and the integrated circuit die 402. In the illustrated example, the conductive metal layer 802 and the adsorbed $H_2O$ layer 804 may collectively comprise the test component 404. It will be appreciated that any suitable adsorbed material may form a film on the conductive metal layer 802 under pressurization to act as a transport media of the test component 404.

Returning to FIG. 3, in some implementations, at 308, the method 300 optionally may include removing the test component from the integrated circuit die under test. The test component may be removed after heating the test assembly in order to allow for the integrated circuit die to be installed in a computing device to computer validate the integrated circuit die. In some implementations, the test component may be removed, and the heat sink may be applied to the backside surface of the integrated circuit die. Alternatively, in some implementations, the test component may remain connected to the integrated circuit under test during computer validation.

At 310, the method 300 includes computer validating the integrated circuit die to determine whether or not the integrated circuit die has the conductive metallic ion diffusion defect. Computer validation of the integrated circuit die under test may be performed by any suitable test computing device. For example, the test computing system 900 shown in FIG. 9 may perform computer validation of the integrated circuit die under test. In some examples, computer validating may include installing the integrated circuit die in a test computing device, and determining that the integrated circuit die has the conductive metallic ion diffusion defect based on the test computing device not being able to be powered on. In some examples, computer validating may include installing the integrated circuit die in a test computing device, and determining that the integrated circuit die has the conductive metallic diffusion defect based on the test computing device producing rendered images having graphical artifacts. In some examples, computer validating may include installing the integrated circuit die in a test computing device, and determining that the integrated circuit die has the conductive metallic ion diffusion defect based on the test computing device producing another type of error. In some examples, computer validating may include in-situ testing in a stress environment with continuous repetitive testing of the integrated circuit die. For example, the integrated circuit die under test may be installed in a test computing device, and the test computing device may be controlled to repeatedly perform processing intensive computing operations. Further, it may be determined that the integrated circuit die has the conductive metallic ion diffusion defect based on the test computing device being unable to produce a desired result or otherwise being unable to perform the computing operations. Further, in some implementations, an integrated circuit die/processor (e.g., 901, 902) may be configured with built-in test functionality to perform functional testing on the die itself without requiring the entire computing system. In some such implementations, it may be determined that the integrated circuit die has the conductive metallic ion diffusion defect based on the built-in test functions in the die/processor (901, 902) outputting an expected test result that indicates that the die is not functioning properly or the die/processor is otherwise unable to perform the self-test properly to produce an expected result.

In some implementations, the methods and processes described herein may be tied to a computing system of one or more computing devices. In particular, such methods and processes may be implemented as a computer-application program or service, an application-programming interface (API), a library, and/or other computer-program product.

Figure 9:
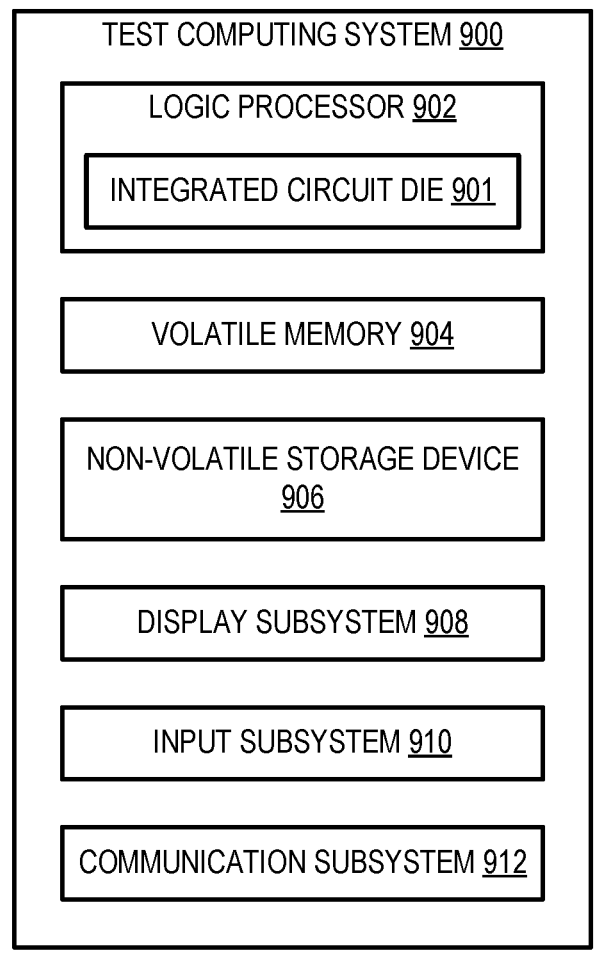
FIG. 9 schematically shows an example test computing system.

FIG. 9 schematically shows a non-limiting implementation of a computing system 900 that can at least partially enact one or more of the methods and processes described above. Computing system 900 is shown in simplified form. Computing system 900 may be used to computer validate an integrated circuit die 901 under test that is installed in the computing system 900 as described above with reference to the validation method illustrated in FIG. 3. Computing system 900 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 900 includes a logic processor 902 volatile memory 904, and a non-volatile storage device 906. Computing system 900 may optionally include a display subsystem 908, input subsystem 910, communication subsystem 912, and/or other components not shown in FIG. 9.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 902 may include one or more physical processors (hardware) configured to execute software instructions. Additionally or alternatively, the logic processor 902 may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor 902 optionally may be distributed among two or more separate devices, which may be remotely located and/or configured for coordinated processing. Aspects of the logic processor 902 may be virtualized and executed by remotely accessible, networked computing devices configured in a cloud-computing configuration. In such a case, these virtualized aspects are run on different physical logic processors of various different machines, it will be understood. In some examples, the integrated circuit die 901 under test may be installed into the logic processor 902 to test the functionality of the integrated circuit die 901 as part of computer validation of the integrated circuit die 901.

Non-volatile storage device 906 includes one or more physical devices configured to hold instructions executable by the logic processors to at least partially implement the methods and processes described herein. When such methods and processes are implemented, the state of non-volatile storage device 906 may be transformed—e.g., to hold different data.

Non-volatile storage device 906 may include physical devices that are removable and/or built-in. Non-volatile storage device 1006 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 906 may include nonvolatile, dynamic, static, read/write, read-only, sequential-access, location-addressable, file-addressable, and/or content-addressable devices. It will be appreciated that non-volatile storage device 906 is configured to hold instructions even when power is cut to the non-volatile storage device 906.

Volatile memory 904 may include physical devices that include random access memory. Volatile memory 904 is typically utilized by logic processor 902 to temporarily store information during processing of software instructions. It will be appreciated that volatile memory 904 typically does not continue to store instructions when power is cut to the volatile memory 904.

Aspects of logic processor 902, volatile memory 904, and non-volatile storage device 906 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 908 may be used to present a visual representation of data held by non-volatile storage device 906. The visual representation may take the form of a graphical user interface (GUI). As the herein described methods and processes change the data held by the non-volatile storage device, and thus transform the state of the non-volatile storage device, the state of display subsystem 908 may likewise be transformed to visually represent changes in the underlying data. Display subsystem 908 may include one or more display devices utilizing virtually any type of technology. Such display devices may be combined with logic processor 902, volatile memory 904, and/or non-volatile storage device 906 in a shared enclosure, or such display devices may be peripheral display devices.

When included, input subsystem 910 may comprise or interface with one or more user-input devices such as a keyboard, mouse, touch screen, or game controller. In some implementations, the input subsystem 910 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 912 may be configured to communicatively couple various computing devices described herein with each other, and with other devices. Communication subsystem 912 may include wired and/or wireless communication devices compatible with one or more different communication protocols. As non-limiting examples, the communication subsystem 912 may be configured for communication via a wireless telephone network, or a wired or wireless local- or wide-area network, such as a HDMI over Wi-Fi connection. In some implementations, the communication subsystem 912 may allow computing system 900 to send and/or receive messages to and/or from other devices via a network such as the Internet.

In an example, a method for validating that an integrated circuit die is not susceptible to a conductive metallic ion diffusion defect comprises applying a test component to a backside surface of the integrated circuit die to form a test assembly. The test component includes a conductive metal layer and a transport media layer for facilitating diffusion of conductive metallic ions. The method further comprises heating the test assembly at a thermal activation temperature, and computer validating the integrated circuit die to determine whether or not the integrated circuit die has the conductive metallic ion diffusion defect. In this example and/or other examples, the method may further comprise pressurizing the test assembly at an increased pressure relative to an ambient pressure while the test assembly is being heated. In this example and/or other examples, the transport media may include adsorbed H2O. In this example and/or other examples, the transport media may include a thermal interface material. In this example and/or other examples, the conductive metal may include copper. In this example and/or other examples, the test component may cover substantially an entire backside surface of the integrated circuit die. In this example and/or other examples, the test assembly may further include a heat sink, and the heat sink may be clamped to the integrated circuit die to compress the conductive metal layer and the transport media layer of the test component to the backside surface of the integrated circuit die. In this example and/or other examples, the conductive metal layer may be applied to the backside surface of the integrated circuit die, and the transport media layer may be applied to the conductive metal layer. In this example and/or other examples, the transport media layer may be applied to the backside surface of the integrated circuit die, and the conductive metal layer may be applied to the transport media layer. In this example and/or other examples, the test assembly may be heated for a designated duration that is selected from a temporal range of 72-120 hours. In this example and/or other examples, the thermal activation temperature may be selected from a thermal range of 100-150 degrees Celsius. In this example and/or other examples, the transport media layer may have a surface area greater than or equal to a surface area of the conductive metal layer. In this example and/or other examples, computer validating may include installing the integrated circuit die in a test computing device, and determining that the integrated circuit die has the conductive metallic ion diffusion defect based on the test computing device not being able to be powered on. In this example and/or other examples, computer validating may include installing the integrated circuit die in a test computing device, and determining that the integrated circuit die has the conductive metallic ion diffusion defect based on the test computing device producing rendered images having graphical artifacts.

In an example, a method for validating that an integrated circuit die is not susceptible to a copper ion diffusion defect comprises applying a test component to a backside surface of the integrated circuit die to form a test assembly. The test component includes a copper layer and a thermal interface material layer for facilitating diffusion of copper ions. The method further comprises heating the test assembly at a thermal activation temperature greater than an operating temperature of the integrated circuit die for a designated duration, removing the test component from the integrated circuit die, and computer validating the integrated circuit die to determine whether or not the integrated circuit die has the copper ion diffusion defect. In this example and/or other examples, the test assembly may further include a heat sink, and the heat sink may be clamped to the integrated circuit die to compress the copper layer and the thermal interface material layer of the test component to the backside surface of the integrated circuit die. In this example and/or other examples, the copper layer may be applied to the backside surface of the integrated circuit die, and the transport media layer may be applied to the thermal interface material layer. In this example and/or other examples, the thermal activation temperature may be selected from a thermal range of 100-150 degrees Celsius. In this example and/or other examples, the designated duration that the test assembly is heated may be selected from a temporal range of 72-120 hours.

In an example, a method for validating that an integrated circuit die is not susceptible to a copper ion diffusion defect comprises applying a test component to a backside surface of the integrated circuit die to form a test assembly. The test component includes a copper layer and a transport media layer for facilitating diffusion of copper ions. The method further comprises heating the test assembly at a thermal activation temperature greater than an operating temperature of the integrated circuit die for a designated duration, pressurizing the test assembly at an increased pressure relative to an ambient pressure while the test assembly is being heated at the thermal activation temperature, removing the test component from the integrated circuit die, and computer validating the integrated circuit die to determine whether or not the integrated circuit die has the copper ion diffusion defect.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for validating that an integrated circuit die is not susceptible to a conductive metallic ion diffusion defect, the method comprising:
   applying a test component to a backside surface of the integrated circuit die to form a test assembly, wherein the test component includes a conductive metal layer and a transport media layer for facilitating diffusion of conductive metallic ions;
   heating the test assembly at a thermal activation temperature; and
   computer validating the integrated circuit die to determine whether or not the integrated circuit die has the conductive metallic ion diffusion defect.

2. The method of claim 1, further comprising:
   pressurizing the test assembly at an increased pressure relative to an ambient pressure while the test assembly is being heated.

3. The method of claim 2, wherein the transport media includes adsorbed $H_2O$.

4. The method of claim 1, wherein the transport media includes a thermal interface material.

5. The method of claim 1, wherein the conductive metal includes copper.

6. The method of claim 1, wherein the test component covers substantially an entire backside surface of the integrated circuit die.

7. The method of claim 1, wherein the test assembly further includes a heat sink, and wherein the heat sink is clamped to the integrated circuit die to compress the conductive metal layer and the transport media layer of the test component to the backside surface of the integrated circuit die.

8. The method of claim 1, wherein the conductive metal layer is applied to the backside surface of the integrated circuit die, and wherein the transport media layer is applied to the conductive metal layer.

9. The method of claim 1, wherein the transport media layer is applied to the backside surface of the integrated circuit die, and wherein the conductive metal layer is applied to the transport media layer.

10. The method of claim 1, wherein the test assembly is heated for a designated duration that is selected from a temporal range of 72-120 hours.

11. The method of claim 1, wherein the thermal activation temperature is selected from a thermal range of 100-150 degrees Celsius.

12. The method of claim 1, wherein the transport media layer has a surface area greater than or equal to a surface area of the conductive metal layer.

13. The method of claim 1, wherein computer validating includes installing the integrated circuit die in a test computing device, and determining that the integrated circuit die has the conductive metallic ion diffusion defect based on the test computing device not being able to be powered on.

14. The method of claim 1, wherein computer validating includes installing the integrated circuit die in a test computing device, and determining that the integrated circuit die has the conductive metallic ion diffusion defect based on the test computing device producing rendered images having graphical artifacts.

15. The method of claim 1, wherein computer validating includes performing a self-test of the integrated circuit die and determining that the integrated circuit die has the conductive metallic ion diffusion defect based on the self-test producing an expected result.

16. A method for validating that an integrated circuit die is not susceptible to a copper ion diffusion defect, the method comprising:
applying a test component to a backside surface of the integrated circuit die to form a test assembly, wherein the test component includes a copper layer and a thermal interface material layer for facilitating diffusion of copper ions;
heating the test assembly at a thermal activation temperature greater than an operating temperature of the integrated circuit die for a designated duration;
removing the test component from the integrated circuit die; and
computer validating the integrated circuit die to determine whether or not the integrated circuit die has the copper ion diffusion defect.

17. The method of claim 16, wherein the test assembly further includes a heat sink, and wherein the heat sink is clamped to the integrated circuit die to compress the copper layer and the thermal interface material layer of the test component to the backside surface of the integrated circuit die.

18. The method of claim 16, wherein the copper layer is applied to the backside surface of the integrated circuit die, and wherein the transport media layer is applied to the thermal interface material layer.

19. The method of claim 16, wherein the thermal activation temperature is selected from a thermal range of 100-150 degrees Celsius and wherein the designated duration that the test assembly is heated is selected from a temporal range of 72-120 hours.

20. A method for validating that an integrated circuit die is not susceptible to a copper ion diffusion defect, the method comprising:
applying a test component to a backside surface of the integrated circuit die to form a test assembly, wherein the test component includes a copper layer and a transport media layer for facilitating diffusion of copper ions;
heating the test assembly at a thermal activation temperature greater than an operating temperature of the integrated circuit die for a designated duration;
pressurizing the test assembly at an increased pressure relative to an ambient pressure while the test assembly is being heated at the thermal activation temperature;
removing the test component from the integrated circuit die; and
computer validating the integrated circuit die to determine whether or not the integrated circuit die has the copper ion diffusion defect.

\* \* \* \* \*